US006740626B2

(12) United States Patent
Neumiller

(10) Patent No.: US 6,740,626 B2
(45) Date of Patent: May 25, 2004

(54) ACIDIC CLEANING FORMULATION CONTAINING A SURFACE MODIFICATION AGENT AND METHOD OF APPLYING THE SAME

(75) Inventor: Phillip J. Neumiller, Racine, WI (US)

(73) Assignee: S.C. Johnson & Son, Inc., Racine, WI (US)

(*) Notice: Subject to any disclaimer, the term of this patent is extended or adjusted under 35 U.S.C. 154(b) by 0 days.

(21) Appl. No.: 08/626,402

(22) Filed: Apr. 2, 1996

(65) Prior Publication Data

US 2003/0109395 A1 Jun. 12, 2003

(51) Int. Cl.$^7$ .............................. C08J 3/03; C11D 9/44; A61K 7/075

(52) U.S. Cl. ....................... 510/109; 510/108; 510/110; 510/122; 524/837; 524/858

(58) Field of Search ................................ 510/109, 108, 510/110, 122, 466, 504, 433; 524/837, 858; 252/FOR 237, FOR 183, FOR 184

(56) References Cited

U.S. PATENT DOCUMENTS

| | | | | |
|---|---|---|---|---|
| 3,249,550 A | | 5/1966 | Metters | |
| 4,005,028 A | | 1/1977 | Heckert et al. | |
| 4,005,030 A | | 1/1977 | Hecker et al. | 250/140 |
| 4,859,359 A | | 8/1989 | DeMatteo et al. | |
| 4,877,654 A | | 10/1989 | Wilson | 427/387 |
| 4,948,531 A | | 8/1990 | Fuggini et al. | 252/544 |
| 5,073,195 A | | 12/1991 | Cuthbert et al. | 106/2 |
| 5,210,253 A | * | 5/1993 | Kinami et al. | 556/448 |
| 5,418,006 A | * | 5/1995 | Roth et al. | 427/154 |
| 5,550,184 A | * | 8/1996 | Halling | 524/837 |
| 5,714,453 A | * | 2/1998 | Neumiller | 510/405 |
| 5,728,758 A | * | 3/1998 | Smith | 524/265 |
| 5,807,921 A | * | 9/1998 | Hill et al. | 524/837 |
| 6,528,580 B1 | * | 3/2003 | Feder et al. | 524/801 |

FOREIGN PATENT DOCUMENTS

| | | | |
|---|---|---|---|
| EP | 0 279 623 A2 | 2/1988 | |
| WO | WO 92/14810 | 9/1992 | |
| WO | WO 92/23804 | 9/1995 | C07F/7/18 |
| WO | WO 95/23804 | 9/1995 | |

* cited by examiner

*Primary Examiner*—Sabiha Qazi

(57) ABSTRACT

An acidic cleaning formulation containing a surface modification agent selected from a group consisting of a hydrolyzed trialkoxysilane or a hydrolyzable quaternary silane and a surfactant is disclosed. The cleaning formulation is stable, provides excellent cleaning efficacy and deposits a silane coating on the surfaces to which it is applied to leave a protective coating thereon. Also, disclosed is a method for applying the cleaning formulation to hard surfaces covered by water.

19 Claims, No Drawings

ACIDIC CLEANING FORMULATION CONTAINING A SURFACE MODIFICATION AGENT AND METHOD OF APPLYING THE SAME

BACKGROUND OF THE INVENTION

1. Field of the Invention

This invention relates to an acidic cleaning formulation containing a surface modification agent selected from the group consisting of a hydrolyzed trialkoxysilane and a hydrolyzable quaternary silane. The formulation is applied to hard surfaces to clean the surface and provide a uniform silane coating on the cleaned surface. The invention also relates to a method for applying the acidic cleaning formulation of this invention to hard surfaces covered by water.

2. Related Background Art

It is known to apply silane cleaning solutions to surfaces to impart water repellency and provide a protective barrier on the treated surface. For example, U.S. Pat. No. 4,948,531 discloses an aqueous cleaning composition comprising (a) one or two nonionic surfactants and an amphoteric surfactant as cleaning agents, (b) lecithin and an aminofunctional polydimethylsiloxane copolymer as protective barrier components, (c) one or two glycols as solvency and grease cutting agents, and (d) water. The disclosed aminofunctional polydimethylsiloxane copolymer has the formula:

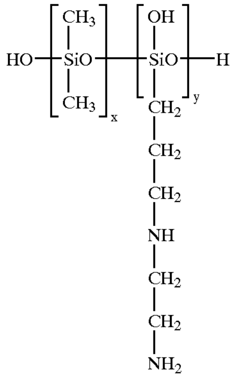

and is available as Dow Corning 531 Fluid (Dow Corning Corporation, Midland, Mich.) which is a 50% solution in aliphatic solvents and isopropyl alcohol. This composition is said to clean a surface and simultaneously leave a protective barrier on the cleaned surface.

U.S. Pat. No. 4,005,030 describes a detergent composition containing an organosilane and an anionic surfactant. The organosilane is said to attach to the hard surfaces to which the detergent composition is applied. U.S. Pat. No. 4,005,025 describes a similar detergent composition containing an organosilane, a water-soluble surfactant and a source of alkalinity. This patent also discloses that the composition preferably contains an amine oxide. However, the composition is said to be unstable when the pH of the composition is not alkaline.

U.S. Pat. No. 4,859,359 is directed to a hard surface cleaning and polishing composition comprising a solvent mixture of a glycol ether, a lower aliphatic alcohol, a hydrocarbon solvent and a minor amount of water together with an organic polysiloxane, a silane and a polycarboxylic chelating acid. The silane compound, which is said to promote the solubility of the other silicone compounds in the mixture, is represented by the formula:

$$R^3—Si(OR4)_3$$

wherein $R^3$ is an alkyl radical containing one to three carbon atoms or phenyl and $R^4$ is an alkyl radical containing one or two carbon atoms. The alkyl trialkoxysilanes are disclosed as preferable.

U.S. Pat. No. 5,073,195 is directed to an aqueous solution of a water silane coupling agent, preferably an amino functional silane coupling agent, and an alkyltrialkoxysilane such as methyltrimethoxysilane or isobutyltrimethoxysilane. The composition is used to treat a surface to impart water repellency to that surface.

Alkoxysilanes are known to hydrolyze upon exposure to water to form reactive silanol groups. The silanol group may then condense with a reactive site on a treated surface. However, if the silanol group is available during storage it may self-condense with other silanol groups to form an insoluble polymer. Hydrolysis of silanes in aqueous medium may be avoided by buffering the emulsions to a specific pH range such as disclosed in U.S. Pat. No. 4,877,654. This patent describes a buffered aqueous silane emulsion containing a hydrolyzable silane that is hydrolytically stable within a determined pH range, an emulsifier having an HLB value of from 1.5 to about 20, a buffering compound and water. However, a buffered composition restricted to a certain pH range can be particularly limiting to a formulator of cleaning compositions.

PCT International Publication No. WO 92/14810 discloses that certain organosilanes containing hydrolyzable groups, especially quaternary ammonium functional organosilanes, can form clear solutions in aqueous media which are stable over extended periods of time by including a water soluble organic, non-silicon quaternary ammonium compound along with nonionic, amphoteric, sarcosine anionic or certain cationic surfactants. The stabilization of hydrolyzable quaternary silanes in the absence of a non-silicon quaternary ammonium compound is not disclosed or suggested. Moreover, the use of hydrolyzed organosilanes is not exemplified.

PCT International Publication No. WO 95/23804 is directed to a hydrolyzed silane obtained by emulsifying a hydrolyzable alkoxysilane represented by the formula:

$$R_f—(CH_2)_p—Si\ \{(—O—CH_2CH_2—)_n—OR')_3$$

wherein $R_f$ is a perfluoroalkyl radical of 3 to 18 carbon atoms, each R' is independently an alkyl radical of 1 to 3 carbon atoms, p is 2 to 4 and n is 2 to 10, with an effective amount of an emulsifier of sufficiently high HLB value to simultaneously retain the hydrolyzable alkoxysilane compound in a substantially totally hydrolyzed state while inhibiting the self-condensation of the hydrolyzed alkoxysilane. Suitable emulsifiers are said to include alkylbenzenesulfonates, linear alkydiphenyletherdisulfonates, alpha-olefin sulfonates, ethoxylated alkyl alcohol ethers, ethoxylated alkyl alcohol ether sulfates, ethoxylated alkylphenols, ethoxylated alkylphenol ether sulfates, ethoxylated perfluoroalkylalkanols, $C_{8-18}$ alkyltrimethylammonium salts, $C_{8-18}$ alkyldimethylammonium salts, ethoxylated $C_{8-18}$ amine salts, alpha-trimethylamino fatty acid betaines and perfluoroalkyl amphoteric surfactants of the type $R_f—CH_2CH(OR")CH_2N(CH_3)2CH_2CO_2$ (inner salt) where R" is H or acetyl, and quaternary salts of the type $R_f—CH_2CH_2SCH_2CH(OH)CH_2N(CH_3)_3^+Cl^-$. According to PCT International Publication No. WO 95/23804, the alkoxysilanes are believed to be hydrolyzed to hydroxysilanes represented by the formula:

$$R_f—(CH_2)—Si—(OH)_3$$

which do not substantially self-condense when the emulsifier is present.

A similar, but non-fluorinated, alkoxysilane aqueous emulsion is TLF-8291, available from E.I. Du Pont de Nemours and Company, Wilmington, Del. TLF-8291 is believed to contain hydrolyzed $C_{18}$-alkyltrialkoxysilane (about 10% by weight of the emulsion) in combination with $C_{8-18}$ tetraalkylammonium chloride (about 30 to 40% by weight of the silane) in water. While the hydrolyzed trialkoxysilane aqueous emulsion appears stable as provided, simple dilution of the aqueous emulsion has been found to give a commercially unacceptable cleaning formulation due to poor cleaning efficacy and silane attachment to glass containers holding such a formulation.

Cleaning formulations containing hydrolyzable quaternary silanes or hydrolyzed trialkoxysilanes, such as TLF-8291, which are stable, avoid substantial silane attacluhent to glass storage containers, provide excellent cleaning, uniform surface deposition after wipe out, and excellent surface wetting and leveling would be highly desirable.

SUMMARY OF THE INVENTION

This invention relates to an acidic cleaning formulation for cleaning hard surfaces comprising: (a) a surface modification agent selected from the group consisting of (i) a hydrolyzed trialkoxysilane in an amount from about 0.00001 to about 10.0 percent by weight of the formulation and (ii) a hydrolyzable quaternary silane in an amount from about 0.00001 to about 10.0 percent by weight of the formulation; (b) a surfactant in an amount from about 0.00001 to about 10.0 percent by weight of the formulation, provided that if the surface modification agent is a hydrolyzable quaternary silane then the surfactant is not a quaternary ammonium compound or sulfobetaine; (c) at least one alcohol having 1 to 12 carbon atoms; and water. Preferably, the hydrolyzed trialkoxysilane is formed in an aqueous emulsion from a hydrolyzable trialkoxysilane compound emulsified in water with about 5 to 100 percent by weight of an emulsifier based on the weight of the hydrolyzable trialkoxysilane and the surfactant is different than the emulsifier. In this preferred embodiment, the emulsifier employed to emulsify the hydrolyzable trialkoxysilane must be in an amount effective to keep the hydrolyzable trialkoxysilane in a substantially totally hydrolyzed state while simultaneously inhibiting appreciable self-condensation of the silane in the aqueous emulsion. The formulation has a pH less than 7.0 which is generally attained by the addition of an acid. Preferably, the alcohol is a mono, di or tri hydric alcohol. The formulation may also include glycol ethers, solvents, fragrances and any other components well known to those skilled in the art of cleaning formulations.

Another embodiment of the present invention is directed to the above-described cleaning formulation having reduced autophobicity, ie., the tendency of the formulation to repel itself after application to a hard surface. It has been surprisingly discovered that the autophobicity of the formulations of the present invention can be reduced by the addition of a siloxane to the formulation. Such siloxanes include, for example, polydimethylsiloxane and derivative thereof.

Yet another embodiment of this invention is directed to a method of applying a surface modification agent to a surface covered by water by adding the above-described acidic cleaning formulation to the water. It has been surprisingly discovered that the surface modification agent of the formulation of this invention attaches to and modifies the surface of substrates, such as glass, ceramic, fiberglass or porcelain, when applied to the water covering such a surface. It has further been discovered that such surface modification occurs even when relatively low levels of the surface modification agents are added to the water covering such surfaces. This method employing the acidic cleaning formulations of this invention may be advantageously employed to clean and protect surfaces covered by water, e.g. toilet bowls, with a minimal use of materials and effort.

The cleaning formulations of this invention are particularly useful for cleaning hard surfaces such as glass, mirrors, tile, ceramic and the like while providing the cleaned surface with a protective silane coating. The formulations of the invention are highly storage stable even when packaged in glass containers, effectively avoid substantial surface attachment of the active silane to the storage container, and thus preserve the active silane for attachment to treated surfaces.

DETAILED DESCRIPTION OF THE INVENTION

This invention is directed to an acidic cleaning formulation which contains a surface modification agent selected from the group consisting of a hydrolyzed trialkoxysilane or a hydrolyzable quaternary silane in a stabilized formulation. The hydrolyzed trialkoxysilane or hydrolyzable quaternary silane are available for attachment to a surface treated with the aqueous acidic cleaning formulations to form a protective barrier which advantageously inhibits the deposition of soils and grease on the treated surface.

The hydrolyzed trialkoxysilane that may be employed in the formulation of this invention is derived from a hydrolyzable trialkoxysilane represented by the formula (I):

$$R^1—CH_2)—Si\{(—O—CH_2CH_2)—OR^2\}_3$$

wherein $R^1$ is selected from the group consisting of a perfluoroalkyl group of 3 to 18 carbon atoms or an alkyl group of 3 to 24 carbon atoms, and $R^2$ is independently an alkyl group having 1 to 3 carbon atoms, p is 0 to 4 and n is 2 to 10. Preferably $R^1$ is an alkyl group of 3 to 24 carbon atoms and p is O, most preferably $R^1$ is an alkyl group having 18 carbon atoms and p is O.

The amount of hydrolyzable trialkoxysilane used in the aqueous emulsion is generally in the range from about 0.00001 to about 25.0 percent by weight of the aqueous emulsion, most preferably from about 0.00001 to about 10.0 percent by weight. Any amount of hydrolyzable trialkoxysilane may be employed in the aqueous emulsion so long as the emulsion is stable prior to its use in preparing the cleaning formulation of this invention.

The hydrolyzed trialkoxysilane may be readily prepared by one of ordinary skill in the art by emulsifying the hydrolyzable trialkoxysilane of formula I in water to form an aqueous emulsion with an emulsifier of sufficiently high HLB value to simultaneously retain the hydrolyzable trialkoxysilane compound in a substantial totally hydrolyzed state and inhibit the hydrolyzed trialkoxysilane compound from appreciable self-condensation. The preparation of aqueous emulsions of hydrolyzed trialkoxysilanes are shown, for example, in PCT International Publication No. WP 95/23804, the disclosure of which is incorporated by reference herein. It may also be possible to form the hydrolyzed trialkoxysilane insitu by the admixture of a hydrolyzable trialkoxysilane with the other components of the formulation of this invention.

If present, the emulsifier generally has an HLB ("The HLB System" published by ICI America's Inc., Wilmington, Del.) value greater than 12. However, when a non-fluorinated trialkoxysilane is employed, then preferably the HLB value of the emulsifier is greater that 16, more preferably greater than 18. Compatible emulsifiers may be used in admixture as long as each meets the above-defined HLB requirements.

Emulsifiers that are preferred for use with a non-fluorinated trialkoxysilane include, without limitation, alkyltrimethylammonium quaternary salts, alkali metal alkylbenzene-sulfonates, linear $C_{12-18}$ alkyldiphenyletherdisulfonates, alpha-olefin sulfonates, alkyl and alkylether sulfates, $C,_{12-18}$ alkyldimethylammonium salts, polyethoxylated $C_{12-18}$ alkylammonium salts and highly ethoxylated alkyl and aryl alcohols. Such emulsifiers include, for example, hexadecyltrimethylammonium 4 chloride, the sodium salt of $C_{14-16}$ alpha olefin sulfonate, octadecylamine-60 E.O. and octadecydimethylammonium chloride.

A particularly preferred emulsifier, particularly for use with a hydrolyzd trialkoxysilane where $R^1$ is a $C_{12}$ to $C_{24}$ alkyl group, is an ethoxylated $C_{8-18}$ amine salt, more preferably tetraalkylammonium chloride, most preferably, having predominantly $C_{16}$-alkyl groups.

Generally, about 5 to 100 percent by weight of an emulsifier based on the weight of the hydrolyzable alkoxysilane is employed in the aqueous emulsion. When $R^1$ is a alkyl group of 3 to 24 carbon atoms then preferably the emulsifier is present in an amount of 10 to 50% based on the weight of the silane, most preferably 30 to 40%. A particularly preferred commercially available hydrolyzed trialkoxysilane emulsion is previously described TLF-8291, available from E.I. Du Pont de Nemours and Company (Wilmington, Del.).

Typically, the aqueous emulsion containing the hydrolyzed trialkoxysilane and emulsifier is present in the cleaning formulation in an amount from about 0.0001 to about 1.0 percent by weight of the cleaning formulation, most preferably from about 0.0001 to about 0.1 percent by weight. The amount of aqueous emulsion used in the cleaning formulation will, of course, depend on the concentration of the hydrolyzed trialkoxysilane in the aqueous emulsion. Thus, any amount of aqueous emulsion may be employed that provides an effective amount of hydrolyzed trialkoxysilane in the cleaning formulation to change the hydrophobicity of a treated surface by surface attachment of the hydrolyzed trialkoxysilane.

Not wanting to be bound by any theory, but so as to provide a full disclosure, it is believed that the hydrolyzed trialkoxysilane is represented by (i) the formula (II):

$$R^1—(CH_2)_p—Si—(OH)_3$$

wherein $R^1$ and p are the same as described for formula I, (ii) by oligomers of formula II or (iii) mixtures thereof. The hydrolyzed trialkoxysilane may form oligomers by the self-condensation of the silanol groups of two or more hydrolyzed trialkoxysilanes so long as the oligomer remains soluble in the aqueous emulsion.

Again, without wishing to be bound by any theory, it is believed that the hydrolyzed trialkoxysilane forms a micelle in conjunction with the emulsifier and that after this aqueous emulsion is diluted into a cleaning formulation the hydrolyzed trialkoxysilane is further protected and stabilized by the addition of the surfactants used in this invention in combination with at least one alcohol having 1–12 carbon atoms and by adjusting the pH of the formulation to an acidic pH. This cleaning formulation allows delivery of the silane to a surface with excellent surface orientation after evaporation of the aqueous carrier. In addition, it is believed that the surfactant inhibits the silane, while in solution, from substantial surface attachment to the storage container and thus preserves the reactive silane for attachment to the treated surface upon application.

The hydrolyzable quaternary silane that may be employed in the formulation of this invention is represented by the formula:

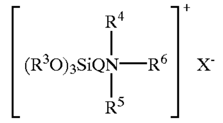

wherein $R^3$ is a hydrolyzable lower alkyl group having 1 to 6 carbon atoms, $R^4$, $R^5$ and $R^6$ are each independently alkyl groups having 1 to 24 carbon atoms, Q is an alkylene radical having 1 to 6 carbon atoms and X is an a halogen. Particulay preferred hydrolyzable quaternary silanes include, without limitation, 3-(trimethoxysilyl) propyldimethyloctadecylammoniumn chloride (available as Dow Corning Q9-6346 Quaternary Silane from Dow Corning Corp., Midland, Mich.) and 3-(trimethoxysilylpropyl) didcylmethylamnnonium chloride (available as Y-11724 Requat Antimicrobial Liquid from Sanitized, Inc., New Preston, Conn.).

When used, the amount of hydrolyzable quaternary silane present in the formulation will range from about 0.00001 to a about 20.0 percent by weight of the formulation, preferably from about 0.00001 to about 10.0 percent by weight of the formulations.

The surfactants employed in the formulation of this invention are selected from the group consisting of: nonionic surfactants such as, for example, linear ethoxylated alcohols (e.g., Neodol® 25-7 (C12-C15 alcohol, EO 7), Neodol® 23-6.5 (C12-C13 alcohol, EO 6.5), Neodol® 1-7 (C12-C13 alcohol, EO 7), Neodol® Neodol® 25-9 (C12-C15 alcohol, EO 9), Neodol® 45-7 (C14-C15 alcohol, EO 7), or Neodol® 91-6 available from Shell Chemical Co., Houston, Tex., Surfonic® L12-8 (C11-C12 alcohol, EO 8), Surfonic® L12-6 (C11-C12 alcohol, EO 6), Surfonic® L24-6.5 (C12-C14 alcohol EO 6.5), Surfonic® L24-7 (C12-C14 alcohol, EO 7), Surfonic® L24-9 (C12-C14 alcohol, EO 9) or Surfonic® 108-83-5 available from Huntsman Corp., Austin, Tex.), alcohol ethoxy carboxylic acids (e.g., Neodox® 23-7, Neodox® 25-6 or Neodox® 45-7) or other nonionic surfactants (e.g., Brij® 76 (polyoxyethylene (20) stearyl ether) or Brij® 97 (polyoxyethylene (10) oleyl ether) available from ICI Americas, Wilmington, Del., Pluronic® L-44 (block copolymers of propylene/ethylene oxide) available from BASF, Parsippany, N.J., Berol® 223 (fatty amine ethoxylate) available from Berol Nobel, Stratford, Conn., and Zonyl® FS-300 (fluoroalkyl alcohol substituted monoether with polyethylene glycol) available from E.I. Du Pont de Nemours and Co., Wilmington, Del.; amphoterics, such as betaines (e.g., Emcol® CC37-18 available from Witco, Houston, Tex., Lonzaine® C or Lonzaine® CO (cocamidopropylbetaines) available from Lonza Inc., Fairlawn, N.J., Mirataine® BB (lauramidopropyl betaine), Mirataine® CB, or Mirataine® Bet C-30 (cocamidopropyl betaines) available from Rhone-Poulenc, Cranbury, N.J., Monateric® CAB available from Mona Chemical Co., Paterson, N.J. and Witco DP 5C-5298-53 (C10 dimethyl betaine) or Witco DP SC-5298-49 (C8 dimethyl betaine) available from Witco), sultaines (e.g., Mirataine® ASC (alkyletherhydroxypropylsultaine) or Mirataine® CBS (cocamidoproylhydroxysultaine) available from Rhone Poulene, Lonzaine® CS or Lonzaine®

(cocoamidopropylhydroxysultaines) available from Lonza Inc., Fairlawn, N.J. and Rewoteric® AM CAS (cocoamidopropylhydroxysultaine) available from Witco), or imidazoline amphoterics (e.g., Amphoterge® W (cocoamphoacetate), Amphoterge® W-2 (cocoamphodiacetate), Amphoterge® K (cocoamphopropionate), Amphoterge® K-2 (cocoamphodipropionate), Amphoterge® L (lauroamphodiacetate), Amphoterge® J-2 or Amphoterge® KJ-2 (capryloamphodipropionate) available from Lonza, Rewoteric® AM V (caprylic glycinate), Rewoteric®AM-KSF (cocoamphopropionate) or Rewoteric® AM 2L (lauroamphodiacetate) available from Witco, Phosphoteric® T-C6 (dicarboxyethyl phosphoethyl imidazoline), Monateric® Cy-Na, or Monateric® LF-Na available from Mona, and Miranol® C2M (cocoamphodiacetate), Miranol® J2M (capryloamphodiacetate), Miranol® JAS (imidazoline amphoteric) available from Rhone-Poulenc); and cationic surfactants such as amine oxides (e.g., Barlox® LF, Barlox® C, Barlox® 105, Barlox® 12, Barlox® 16S, or Barlox® 18S available from Lonza, Rhodamox® LO or Rhodamox® CO available from Rhone-Poulenc and Varox® 305 or Varox® 743 available from Witco), and quaternary cationic surfactants (e.g., Bardec® 208M or Barquat® 42802 available from Lonza and BTC 835 available from Stephan, Co., Northfield, Ill.), or dialkoxy alkyl quaternaries (e.g., Variquat® 66, Variquat® K-1215, Adogen®D 444, Adogen® 461 or Adogen® 462 available from Witco).

If the surface modification agent is a hydrolyzable quaternary silane then the surfactant is not a quaternary ammonium compound or sulfobetaine. The preferred surfactants for use with the hydrolyzable quaternary silanes are amphoteric betaines or amine oxides. For a trialkoxysilane surface modification agent, the preferred surfactants employed in the cleaning formulation of this invention include amine oxides, amphoteric sultaines, amphoteric betaines and quaternary cationic surfactants, most preferably amine oxides such as Lonza Barlox® 12 and amphoteric betaines such as Lonzane® CO.

The particularly preferred amine oxides are represented by the formula:

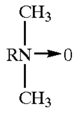

wherein R is a $C_8$ to $C_{16}$ alkyl group. Most preferably R is a $C_{12}$ alkyl group.

If the formulation contains a trialkoxysilane, then the surfactant employed in the formulation of this invention will differ from the emulsifier described above. At least one surfactant must be present, although, it may be preferable to employ more than one surfactant.

Generally, a surfactant or mixture of surfactants will be present in the formulation in an amount from about 0.00001 to about 10 percent by weight of the formulation, more preferably in an amount from about 0.0001 to about 5 percent by weight of the formulation and most preferably in an amount from about 0.0001 to about 3 percent by weight of the formulation. However, any amount of surfactant may be employed that provides a formulation that contains a stabilized hydrolyzed trialkoxysilane or a stabilized hydrolyzable quaternary silane and which has good cleaning properties.

The formulation of this invention contains at least one alcohol having 1 to 12 carbon atoms that are preferably selected from mono, di and tri hydric alcohols. Such mono, di and tri hydric alcohols include, for example, ethanol, propanol, hexanol, isopropanol, N-pentanol, propylene glycol, glycerin, 2-pentanol, 3-pentanol, 2-butanol, diethylene glycol, Neodol® 91 ($C_9$-$C_{11}$ primary alcohol), Neodol® 1 ($C_{11}$ primary alcohol) and decyl alcohol. Generally, the concentration of the mono, di or tri hydric alcohols in the formulation is in a range from about 0.00001 to about 5.0 percent by weight of the formulation. The amount of alcohol employed in the formulation of this invention should be maintained below that amount which would cause substantial alkylation of the hydrolyzed trialkoxysilane.

Besides the alcohols described above, the formulations of this invention may also include other solvents, such as glycol ethers, to assist in cleaning the treated surface. Typical glycol ethers include, without limitation Dowanol® EB, (ethylene glycol n-butyl ether), Dowanol® DB (diethylene glycol n-butyl ether), Dowanol® PnB (propylene glycol n-butyl ether), Dowanol® DPnB (dipropylene glycol n-butyl ether), Dowanol® PPH (propylene glycol phenyl ether), Dowanol® PMA (propylene glycol methyl ether acetate), Dowanol® EPH (ethylene glycol phenyl ether), Dowanol® DPMA (dipropylene glycol methyl ether acetate), Dowanol® DPM (dipropylene glycol methyl ether), Dowanol® PnP (propylene glycol n-propyl ether), Witco® DM-55 (polyethylene glycol dimethyl ether) and the like. If employed, the glycol ethers are generally present in the formulation in an amount from about 0.1 to about 6.0 percent by weight of the formulation.

The formulations of this invention typically include an acid to ensure that the pH of the formulation is less than 7, and preferably from about 0.5 to about 6.95, most preferably about 0.75 to about 5. Generally, such an acid is present in an amount from about 0.00001 to about 7.5 percent by weight of the formulation. Exemplary acids include, without limitation, glycolic acid, lactic acid, acetic acid, sulfamic acid, citric acid and gluconic acid. Glycolic acid and lactic acid are preferred.

Additional adjuvants which may be employed in the formulations of this invention include fragrances, colorants and the like. The use of such adjuvants is well known to those of ordinary skill in the art.

The preparation of the cleaning formulations will vary depending on the surface modification agent employed. For example, if the surface modification agent is a quaternary silane then it is preferred to first add the surfactant to water followed by the addition of the agent. Thereafter, any solvents; bases or other adjuvants may be added to the formulations. It has been surprisingly discovered that the activity of the hydrolyzable quaternary silane is better preserved when using the method of preparation described above, while the addition of the hydrolyzable quaternary silane after mixing the other formulation components may result in a loss of activity for the surface modification agent. On the other hand, when employing a hydrolyzed trialkoxysilane, it is most peferable to add the silane last to the completed formula.

In yet another embodiment of this invention, a siloxane is added to the above described cleaning formulation to reduce the autophobicity of those formulations. The siloxanes that may be employed include polydimethyl-siloxane and derivatives thereof. Such derivatives may include, for example, polyalkylene oxide-modified polydimethylsiloxanes represented by the formula $$(CH_3)_3SiO((CH_3)_2SiO)_x(CH_3\underset{\displaystyle PE}{\underset{|}{Si}}O)_ySi(CH_3)_3$$

wherein PE is represented by $—CH_2CH_2CH_2O(EO)_m(PO)_nZ$ wherein EO is ethyleneoxy, PO is 1,2-propyleneoxy and Z is hydrogen or a lower alkyl group, or $$(CH_3Si)_{y-2}[(OSi(CH_3)_2)_{x/y}\ O\text{-}PE']_y$$

wherein PE' is represented by $—(EO)_m(PO)_nR$ wherein EO and PO are the same as described above and R is a lower alkyl group.

Other siloxanes which may be useful for reducing autophobicity include aromatic substituted siloxanes such as diphenyldimethylsiloxane copolymers, phenylmethylsiloxane polymers and methyl (propyl hydroxide, ethoxylated) bis (trimethylsiloxy) silane (Dow Corning® Q2-5211, available from Dow Corning, Midland, Mich.).

If present, the siloxane is employed in an amount effective to reduce the autophobicity of the cleaning formula. Generally, about 0.00001 to about 0.5 percent of siloxane by weight of the formulation may be added to inhibit autophobicity. However, any amount of siloxane that is effective to inhibit autophobicity is encompassed by the present invention.

This invention is also directed to a method of applying a surface modification agent to a hard surface, such as glass, ceramic, fiberglass or porcelain, that is covered by water. The above-described acidic cleaning formulation is added directly to the water in an amount effective to modify the surface covered by the water through attachment of the surface modification agent, i.e., the silane, to that surface.

Without being bound to theory, it is believed that the silane contained in the formulation of this invention has a preferred orientation for liquid/air or liquid/solid surfaces. After the acidic cleaning formulation is introduced to the water, it is believed that the surface modification agent, i.e., the hydrolyzed trialkoxysilane or hydrolyzable quaternary silane, is no longer stabilized to inhibit surface attachment and that the reactive silane migrates to the liquid/solid interface and adheres to the surface. It has been surprisingly discovered that surface modification can be obtained with as little as 0.1 ppm to 100 ppm of surface modification agent in the water.

The method of this invention can be readily practiced, for example, by the addition of an effective amount of the acidic cleaning formulation to water contacting the surface which is to be treated. The amount of acidic cleaning formulation that is added to the water is dependent on the concentration of surface modification agent in the formulation, the amount of water contacting the surface and the surface area that is to be coated. Generally, the amount of acidic cleaning formulation added to the water is an amount that will provide at least about 0.1 ppm of surface modification agent in the water. The acidic cleaning formulation may be added to the water in any manner desired, such as by direct application or by a slow release mechanism, e.g., a toilet bowl tank dispenser.

The Examples which follow are intended as an illustration of certain preferred embodiments of the invention, and no limitation of the invention is implied.

EXAMPLE 1

A cleaning formulation was prepared containing the following components (as used herein % w/w means the percent weight of the component based on the weight of the formulation unless otherwise specified):

| Components | % w/w |
|---|---|
| Lonza ® CO (amphoteric betaine)[1] | 3.000 |
| Glycerin | 0.100 |
| Isopropyl Alcohol | 1.000 |
| Deionized Water | 88.100 |
| Lactic Acid | 6.800 |
| TLF-829[2] | 1.000 |
| | 100.000 |

[1] $C_6$–$C_{13}$ amphoteric betaine
[2] 10% $C_{18}$-alkyltrialkoxyl silane with $C_{16}$-tetralkylammonium chloride (30 to 40% based on the silane) in an aqueous emulsion available from E.I. Du Pont de Nemours & Co., Wilmington, Delaware

EXAMPLE 2

A cleaning formulation was prepared in a manner similar to Example 1, except the surface modification agent was Dow Corning Q9-6346 (72%) available from Dow Coming, Midland, Mich.

EXAMPLE 3

The cleaning formulation was prepared in a manner similar to Example 1, except the surface modification agent was Requat 2-C10, available from Sanitized Inc., New Preston, Conn.

EXAMPLE 4

A cleaning composition was prepared having the following components:

| Components | % w/w |
|---|---|
| Lonza Lonzaine ® CO[1] | 3.000 |
| Shell Neodox ® 25-6[2] | 2.000 |
| Shell Neodol ® 25-7[3] | 0.500 |
| Glycerin | 0.300 |
| Isopropyl Alcohol | 1.000 |
| Witco ® DM 55[4] | 1.000 |
| Dow Triad[5] | 1.000 |
| Fragrance | 0.150 |
| Dow Corning ® Q2-5211[6] | 0.010 |
| Deionized Water | 84.040 |
| Citric Acid | 3.000 |
| Sulfamic Acid 98% | 3.000 |
| TLF-8291 | 1.000 |
| | 100.000 |

[1] $C_6$–$C_{18}$ amphoteric betaine (cocamidopropyl betaine)
[2] alcohol ethoxycarboxylic acid
[3] $C_{12}$–$C_{15}$ linear ethoxylated alcohol
[4] polyethylene glycol dimethyl ether
[5] Equal parts of Dowanol ® PnP, DPM and PnB
[6] siloxane This formulation was found to clean (rust and manganese) stains on porcelain and to deposit the active silane under water. The pH of the solution was 1.05.

EXAMPLE 5A

A cleaning formulation having the following components was prepared.

| Components | % w/w |
|---|---|
| Neodol ® 25-7 | 4.000 |
| Lonzaine ® CO | 3.000 |
| Dow Triad | 1.950 |
| Glycerin | 0.140 |
| Isopropyl Alcohol | 3.000 |
| Isopar E[1] | 1.000 |
| Witco ® DM55 | 4.000 |
| Fragance | 0.250 |
| Deionized Water | 75.350 |
| Dow Corning ® Q2-5211 | 0.010 |
| Lactic Acid | 6.800 |
| TLF-8291 | 0.500 |

[1]Isoparaffinic Hydrocarbon

This cleaning formulation had a pH of about 2.

EXAMPLE 5B

A cleaning formulation having the following components was prepared:

| Components | % w/w |
|---|---|
| Deionized Water | 82.795 |
| Lactic Acid | 5.500 |
| Lonzaine ® CO | 2.250 |
| Neodol ® 25-7 | 2.850 |
| Witco ® DM 55 | 1.000 |
| Glycerin | 0.100 |
| Isopropyl Alcohol | 4.000 |
| Isopar E | 0.900 |
| Dow-Corning ® Q2-5211 | 0.005 |
| Fragrance | 0.200 |
| TLF-8291 | 0.400 |

This cleaning formulation provided excellent cleaning efficacy and stability.

EXAMPLE 6

A cleaning formulation having the following components was prepared.

| Components | % w/w |
|---|---|
| Barlox LF[1] | 0.250 |
| Isopropyl Alcohol | 3.000 |
| Neodox 25-6[2] | 0.100 |
| Dow Triad | 1.000 |
| Fragance | 0.050 |
| n-hexanol | 0.075 |
| Deionized Water | 94.965 |
| Dow Corning ® Q2-5211 | 0.010 |
| Lactic Acid (85%) | 0.200 |
| TLF-8291 | 0.350 |

[1]Amine oxide
[2]$C_{12}$–$C_{15}$ alcohol ethoxycarboxylic acid

EXAMPLE 7

A cleaning formulation having the following components was prepared.

| Components | % w/w |
|---|---|
| Lonza Barlox ® 12 (amine oxide) | 0.500 |
| Lonzaine ® CO (amphoteric surfactant) | 0.500 |
| Propylene Glycol | 1.500 |
| Isopropyl Alcohol | 2.000 |
| Dowanol ® PnP | 1.000 |
| Dowanol ® PnB | 1.000 |
| Dowanol ® DPM | 1.000 |
| Fragance | 0.060 |
| n-hexanol | 0.200 |
| Deionized Water | 84.063 |
| Glycolic Acid (70%) | 7.170 |
| TLF-8291 | 1.000 |
| Colorant | 0.007 |

The pH of the resulting formulation was 2.21.

EXAMPLES 8–9

Cleaning formulations were prepared having substantially the same composition as Example 7, except that the amine oxide was Lonza Barlox® LF and Lonza Barlox® 10-S, respectively. The cleaning formulation of Example 9 had a pH of 2.21.

EXAMPLES 10–29

Cleaning formulations were prepared having substantially the same composition of Example 7, except that the Lonzaine® CO amphoteric surfactant was replaced with the one of the amphoteric surfactants described below.

| Example | Amphoteric Surfactant | pH |
|---|---|---|
| 10 | Lonzaine ® C | 2.27 |
| 11 | Mirataine ® BB | 2.21 |
| 12 | DP SC-5298-49 | 2.19 |
| 13 | DP SC-5298-53 | 2.30 |
| 14 | Lorizaine ® CS | 2.20 |
| 15 | Lonzaine ® JS | 2.13 |
| 16 | Mirataine ® ACS | 2.18 |
| 17 | Mirataine ® CBS | 2.25 |
| 18 | Rewoteric ® AM CAS | 2.28 |
| 19 | Amphoterge ® K | 2.32 |
| 20 | Amphoterge ® K-2 | 2.23 |
| 21 | Amphoterge ® KJ-2 | 2.90 |
| 22 | Amphoterge ® L-Special | 2.20 |
| 23 | Amphoterge ® W | 2.27 |
| 24 | Amphoterge ® W-2 | 2.32 |
| 25 | Miranol ® C2M Conc. NP | 2.24 |
| 26 | Miranol ® J2M Conc. | 2.18 |
| 27 | Rewoteric ® Am KSF-40 | 2.29 |
| 28 | Rewoteric ® AMV | 2.34 |
| 29 | Rewoteric ® AM 2L-40 | 2.34 |

EXAMPLES 30–41

Cleaning formulations were prepared having substantially the same composition as Example 7, except the Lonzaine® CO amphoteric surfactant was replaced by one of the nonionic surfactants described below:

| Example | Nonionic surfactants | pH |
|---|---|---|
| 30 | Zonyl ® FS 300 | 2.34 |
| 31 | Neodox ® 25-6 | 2.37 |

-continued

| Example | Nonionic surfactants | pH |
|---|---|---|
| 32 | Surfonic ® L 24-7 | 2.42 |
| 33 | Neodox ® 45-7 | 2.31 |
| 34 | Pluronic ® L-44 | 2.41 |
| 35 | Surfonic ® L 12-8 | 2.37 |
| 36 | Neodol ® 45-7 | 2.25 |
| 37 | Neodol 25-7 | 2.35 |
| 38 | Neodol ® 23-6.5 | 2.24 |
| 39 | Surfonic ® L 12-6 | 2.37 |
| 40 | Berol ® 223 | 2.27 |
| 41 | Neodol ® 1-7 | 2.37 |

EXAMPLES 42–49

Cleaning formulations were prepared having substantially the same composition as Example 7, except the mixture of glycol ethers (PnP, PnB and DPM) were replaced by an identical amount of the glycol ethers described below.

| Example | Glycol ether | pH |
|---|---|---|
| 42 | DB (diethylene glycol n-butyl ether) | 2.33 |
| 43 | PnB (propylene glycol n-butyl ether) | — |
| 44 | DPnB (dipropylene glycol n-butyl ether) | — |
| 45 | PPh (propylene glycol phenyl ether) | — |
| 46 | DPM (dipropylene glycol methyl ether) | 2.37 |
| 47 | PnP (propylene glycol n-propyl ether) | 2.31 |
| 48 | Witco DM-55 (polyethylene glycol dimethyl ether) | 2.35 |
| 49 | EB (ethylene glycol n-butyl ether) | 2.25 |

EXAMPLES 50–55

Cleaning formulations were prepared having substantially the same components as Example 7, except the n-hexanol was replaced by the alcohols listed below.

| Example | Alcohol | pH |
|---|---|---|
| 50 | ethanol | 2.30 |
| 51 | propanol | 2.02 |
| 52 | pentanol | 2.26 |
| 53 | glycerin | 2.28 |
| 54 | 2-pentanol | 2.32 |
| 55 | diethylene glycol | 2.32 |

EXAMPLES 56–57

Two cleaning formulations were prepared having a composition similar to Example 7, except that the isopropanol was replaced by ethanol and propanol, respectively. Examples 56 and 57 had a pH of 2.27 and 2.30, respectively.

EXAMPLES 58–62

Cleaning formulations were prepared having a composition similar to Example 7, except that the glycolic acid was replaced by the following acids in the amounts set forth below.

| Example | Acid | % w/w | pH |
|---|---|---|---|
| 58 | Lactic Acid (80%) | 6.274 | 2.30 |
| 59 | Citric Acid (99.5%) | 5.044 | 2.24 |
| 60 | Sulfamic Acid (98%) | 1.000 | 1.42 |
| 61 | Gluconic Acid (50%) | 10.038 | 2.82 |
| 62 | Acetic Acid (30%) | 6.670 | 3.39 |

EXAMPLES 63–64

Two cleaning formulations were prepared having a composition similar to Example 7, except the amine oxide (Lonza Barlox® 12) was replaced by Lonza Barlox® 16-S and Lonza Barlox® 18-S, respectively. Examples 63 and 64 had a pH of 2.20 and 2.32, respectively.

EXAMPLE 65

A cleaning formulation having the following components was prepared.

| Components | % w/w |
|---|---|
| Shell Neodol ® 25-7 | 4.000 |
| Lonzaine ® CO | 3.000 |
| Dowanol ® DPM | 0.650 |
| Dowanol ® PnB | 0.650 |
| Dowanol ® PnP | 0.650 |
| Isopropyl Alcohol | 1.000 |
| Witco DM-55 | 5.000 |
| Deionized Water | 77.250 |
| Lactic Acid (88%) | 6.800 |
| TLF-8291 | 1.000 |

The formulation had a pH of 2.30.

EXAMPLES 66–86

Cleaning formulations were prepared having a composition similar to Example 65, except the surfactant Lonzaine® CO was replaced by the following surfactants in the amounts set forth below.

| Examples | Surfactant | % w/w | pH |
|---|---|---|---|
| 66 | Lonzaine ® C | 3.000 | 2.25 |
| 67 | Mirataine ® BB | 3.500 | 2.29 |
| 68 | DP SC-5298-49 | 2.941 | 2.38 |
| 69 | DP SC-5298-53 | 2.830 | 2.34 |
| 70 | Lonzaine ® CS | 2.100 | 2.14 |
| 71 | Mirataine ® ASC | 2.442 | 2.08 |
| 72 | Lonzaine ® JS | 2.143 | 2.16 |
| 73 | Mirataine ® CBS | 2.386 | 2.14 |
| 74 | Rewoteric ® AM CAS-15U | 2.100 | 2.17 |
| 75 | Amphoterge ® K | 2.838 | 2.84 |
| 76 | Amphoterge ® K-2 | 2.625 | 2.85 |
| 77 | Amphoterge ® KJ-2 | 2.625 | 2.90 |
| 78 | Amphoterge ® L-Special | 2.838 | 2.56 |
| 79 | Amphoterge ® W | 2.283 | 2.60 |
| 80 | Amphoterge ® W-2 | 2.100 | 2.55 |
| 81 | Miranol ® C2M Conc. NP | 2.763 | 2.61 |
| 82 | Miranol ® J2M Conc. | 2.763 | 2.67 |
| 83 | Rewoteric ® AM KSF | 2.625 | 2.86 |
| 84 | Rewoteric ® AM V | 3.000 | 2.61 |
| 85 | Rewoteric ® AM2L | 2.100 | 2.56 |
| 86 | Mona Phosphoteric T-C6 (40%) | 2.625 | 2.78 |

-continued

| Examples | Surfactant | % w/w | pH |
|---|---|---|---|

Note: Any difference in percent weight of the surfactant compound to that used in Example 65 was offset by the amount of deionized water used.

EXAMPLES 87–97

Cleaning formulations were prepared having a composition similar to Example 65, except the nonionic surfactant Shell Neodol® 25-7 was replaced by the following surfactants in the amounts set forth below.

| Example | Surfactant | % w/w | pH |
|---|---|---|---|
| 87 | Neodol ® 1-7 | 4.000 | 2.35 |
| 88 | Neodol ® 23-6.5 | 4.000 | 2.37 |
| 89 | Neodol ® 25-7 | 4.000 | — |
| 90 | Neodol ® 45-7 | 4.000 | 2.37 |
| 91 | Surfonic ® L12-8 | 4.000 | 2.28 |
| 92 | Surfonic ® L12-6 | 4.000 | 2.38 |
| 93 | Surfonic ® L24-7 | 4.000 | 2.38 |
| 94 | Neodox ® 25-6 | 4.444 | 2.49 |
| 95 | Neodox ® 45-7 | 4.444 | 2.35 |
| 96 | Pluronic ® L44 | 4.000 | 2.38 |
| 97 | Berol ® 223 | 4.000 | 2.47 |

EXAMPLE 98

A cleaning formulation was prepared having a composition similar to Example 65, except 0.25% w/w of Zonyl® FS-300 (fluoroalkyl alcohol substituted monether with polyethylene glycol available from E.I. Du Pont de Nemours & Co., Wilmington, Del.) was added to the formulation. The formulation had a pH of 2.41.

EXAMPLES 99–106

Cleaning formulations were prepared having a composition similar to Example 65, except the glycol ethers (DPM, PnB, PnP and Witco DM-55) were replaced by 6.95% w/w of the following glycol ethers.

| Example | Glycol ether | pH |
|---|---|---|
| 99 | Dowanol ® EB (ethylene glycol n-butyl ether) | 2.33 |
| 100 | Dowanol ® DB (diethylene glycol n-butyl ether) | 2.44 |
| 101 | Dowanol ® PnB (propylene glycol n-butyl ether) | — |
| 102 | Dowanol ® DPnB (dipropylene glycol n-butyl ether) | — |
| 103 | Dowanol ® PPh (propylene glycol phenyl ether) | — |
| 104 | Dowanol ® DPM (dipropylene glycol methyl ether) | 2.44 |
| 105 | Dowanol PnP (propylene glycol n-propyl ether) | 2.46 |
| 106 | Witco Varonic ® DM-55 (polyethylene glycol dimethyl ether) | 2.45 |

EXAMPLES 107–114

Cleaning formulations were prepared having a composition similar to Example 65, except the isopropanol was replaced by one of the following alcohols.

| Example | Alcohol | pH |
|---|---|---|
| 107 | diethylene glycol | 2.23 |
| 108 | ethanol | 2.26 |
| 109 | glycerin | 2.26 |
| 110 | hexanol | 2.28 |
| 111 | pentanol | 2.30 |
| 112 | 2-pentanol | 2.31 |
| 113 | propanol | 2.33 |
| 14 | propylene glycol | 2.34 |

EXAMPLES 115–119

Cleaning formulations were prepared having a composition similar to Example 65, except the lactic acid was replaced by the following acids in the amounts set forth below.

| Example | Acid | % w/w | pH |
|---|---|---|---|
| 115 | Glycolic acid | 8.260 | 1.96 |
| 116 | Gluconic acid (40–50%) | 12.840 | 2.35 |
| 117 | Citric acid (99.5+%) | 5.780 | 1.93 |
| 118 | Acetic acid (30%) | 6.670 | 2.94 |
| 119 | Sulfamic acid (98%) | 0.500 | 1.63 |

EXAMPLES 120–121

Two cleaning formulations were prepared having compositions similar to Example 65, with the exceptions that Shell Neodol® 25-7 was replaced in both compositions by Surfonic® L12-8, and Lonzaine® CO was replaced b)y 2.625% w/w of Rewoteric® Am KSF-40 and Mona Phosphoteric® T-C6, respectively. Example 121 had a pH of 2.40.

EXAMPLE 122

A cleaning formulation having the following components was prepared.

| Example | % w/w |
|---|---|
| Surfonic ® L12-8 | 4.000 |
| Lonza Lonzaine ® CO | 3.000 |
| Dowanol ® DPM | 6.950 |
| Isopropanol | 1.000 |
| Deionized Water° | 77.250 |
| Lactic acid (88%) | 6.800 |
| TLF-8291 | 1.000 |

The formulation had a pH of 2.10.

Stability Testing

Two ounce samples of each formula were placed in a 100° F. (about 38° C.) oven. Each sample was visually monitored for up to a month. The results of these tests are set forth in Table 1. The preferred formulations of this invention remained clear, only slightly cloudy or swirly after two weeks to a month of observation.

Hydrophobicity Testing

Hydrophobicity of each formula was measured using a water drop test. This test measures how well a formulation exhibits sheeting of water. The test was conducted by first cleaning a mirror plate (12 $in^2$ (about 77 $cm^2$) Mirror Model #P1212-NT, Monarch Mirror Co.) with HPLC grade acetone and a paper towel. Next, the mirror was rinsed with deionized water and blown dry. The mirror was then divided into 6 equivalent sections and about 0.15 to 0.25 g of a formula was applied to a section and wiped completely dry with half of a paper towel. After waiting one half hour, a pipette was used to deliver five drops of room temperature tap water to each section and to a control section, i.e., a section of the mirror to which a formula was not applied. After 5 minutes each drop's diameter was measured parallel to the base of the mirror. An average drop size was calculated for each formula and the control.

The average drop size for the controls was 0.79 cm. The preferred formulas of this invention exhibited an improvement over the control. The results of the water drop test are set forth in Table 1.

Sliding Drop Test

The sliding drop test, which quantifies how a droplet flows or wets an inclined surface, was conducted on several of the formulations of this invention. The test was conducted on a 6 $in^2$ (about 15 $cm^2$)glazed ceramic tile (Tilepak Glossy White CC-100), which was first cleaned with warm tap water and wiped dry. Each tile was treated with an equivalent amount of formulation (two to ten drops) and wiped dry. After ten minutes, a ceramic tile was placed on an incline and a Gilson Pipetman was used to dispense a 50 $\mu$L drop on each tile. The trail left on the tile was observed and rated on a scale of 0–5 as follows:

0—indicates a continuous even trail the same width as the drop;

1—indicates a continuous trail narrower than the drop;

2—indicates a trail that is occasionally broken and narrower than the drop;

3—indicates a trail with only half the trail wetted;

3.5—indicates that elongated drops cover a quarter of the trail;

4—indicates that spherical drops cover a quarter of the trail;

4.5—indicates that the trail consists of only a few scattered spherical drops; and 5—indicates the drop rolls off the tile leaving no trail.

The results of this test are set forth in Table 2.

Cleaning Tests

A cotton swab cleaning test was also utilized to test the cleaning efficacy of the formulations of this invention, versus interior soil, shell soil and beef tallow.

Interior soil was prepared by adding and melting together 0.5 g of synthetic sebum, 0.5 g of mineral oil, and 0.5 g clay, followed by the addition of 98.5 g of 1,1,1-trichloroethane. (Synthetic sebum consists of: 10% palmitic acid; 5% stearic acid; 15% coconut oil; 10% paraffin wax; 15% cetyl esters wax; 20% olive oil: 5% squalene; 5% cholesterol; 10% oleic acid; and 5% linoleic acid which are added together and heated over low heat in order to melt the solids and form a homogeneous mixture.) Shell soil consists of 40 parts Metallic Brown Oxide (Pfizer B-3881); 24 parts Kerosene (deodorized); 24 parts Shell sol 340; 2 parts White Mineral Oil; 2 parts Shell Tellus 27; and 2 parts Hydrogenated Vegetable Oil(Crisco). The Shell soil was prepared by dissolving vegetable shortening (Crisco) in kerosene and Shell Sol 340, Next, mineral oil, Shell Tellus 27 and pigment were added followed by agitating continuously for two hours.

A mirror plate, like that employed in the hydrophobicity test, was cleaned with Classical EB Windex® and thoroughly dried with a paper towel. The soils were applied to the mirrors. After 24 hours, a cotton swab was dipped into the formulations and wiped horizontally in a constant motion ten cycle pattern, about one inch (2.54 cm) long, with a constant pressure. After the cleaned areas were dry, the effectiveness of each formula was rated on a scale of one to ten, with one representing no soil removal. The results of the cleaning tests on the formulations of this invention are set forth in Table 1.

TABLE 1

| Ex. | Drop Tests | Cleaning Test Interior | Shell | Beef Tallow | Appearance at 100° F. (about 38° C.) for 2 weeks (Exs. 7–64) for 1 month (Exs. 1–6 & 65–122) |
|---|---|---|---|---|---|
| 1 | 0.80 | 9 | 6 | 8.5 | clear |
| 2 | 0.63 | 7.0 | 7 | 9.0 | clear |
| 3 | 0.83 | 6.0 | 6 | 9.0 | clear |
| 4 | 0.67 | 8.0 | 7 | 5.0 | clear yellow |
| 5A | 0.73 | 5.0 | 8 | 7.0 | slight haze |
| 6 | 0.83 | 9.0 | 6 | 10.0 | slight haze |
| 7 | 0.70 | 6.1 | 5.0 | 6.8 | clear |
| 8 | NT | NT | NT | NT | unstable |
| 9 | 0.79 | 6.0 | 5.0 | 8.0 | very hazy |
| 10 | 0.79 | 6.0 | 7.0 | 7.0 | clear |
| 11 | 0.78 | 6.0 | 7.0 | 6.0 | clear |
| 12 | 0.80 | 7.0 | 6.5 | 8.0 | slightly hazy |
| 13 | 0.83 | 7.0 | 6.0 | 7.0 | very slightly hazy |
| 14 | 0.82 | 6.0 | 6.0 | 7.0 | unstable |
| 15 | 0.85 | 7.0 | 7.0 | 7.0 | hazy |
| 16 | 0.83 | 7.0 | 6.0 | 7.0 | hazy |
| 17 | 0.83 | 7.0 | 7.0 | 6.0 | very slightly hazy |
| 18 | 0.66 | 6.0 | 7.0 | 7.0 | v.s. hazy |
| 19 | 0.69 | 6.0 | 7.0 | 5.0 | clear |
| 20 | 0.67 | 7.0 | 7.0 | 6.0 | clear |
| 21 | 0.83 | 6.0 | 6.0 | 7.0 | clear |
| 22 | 0.68 | 7.0 | 7.5 | 8.0 | hazy |
| 23 | 0.74 | 6.0 | 7.5 | 7.0 | very slightly hazy |
| 24 | 0.72 | 8.0 | 6.5 | 8.0 | hazy |
| 25 | 0.69 | 7.5 | 6.5 | 9.0 | unstable |
| 26 | 0.74 | 8.5 | 6.5 | 8.0 | unstable |
| 27 | 0.71 | 6.0 | 6.5 | 9.0 | clear |
| 28 | 0.75 | 7.0 | 6.5 | 8.0 | very hazy |
| 29 | 0.68 | 6.0 | 6.5 | 7.0 | unstable |
| 30 | 0.71 | 6.0 | 4.0 | 5.5 | clear |
| 31 | 0.79 | 5.0 | 5.0 | 5.0 | very slightly hazy |
| 32 | 0.74 | 5.0 | 5.0 | 5.0 | clear |
| 33 | 0.77 | 6.0 | 5.0 | 4.5 | very slightly hazy |
| 34 | 0.88 | 5.0 | 4.0 | 4.0 | clear |
| 35 | 0.74 | 6.0 | 5.0 | 4.5 | clear |
| 36 | 0.77 | 6.0 | 6.0 | 4.5 | clear |
| 37 | 0.76 | 5.0 | 4.0 | 4.5 | clear |
| 38 | 0.73 | 6.0 | 3.0 | 4.0 | clear |
| 39 | 0.76 | 6.0 | 4.0 | 7.0 | very slightly hazy |
| 40 | 0.67 | 7.0 | 4.0 | 6.0 | very slightly hazy |
| 41 | 0.71 | 7.0 | 5.0 | 6.5 | clear |
| 42 | 0.68 | 6.0 | 4.0 | 6.5 | clear |
| 43 | NT | 6.0 | 3.0 | 4.0 | unstable |
| 44 | NT | NT | NT | NT | unstable |
| 45 | NT | NT | NT | NT | unstable |
| 46 | 0.70 | 6.0 | 5.0 | 5.0 | clear |
| 47 | 0.72 | 6.0 | 6.0 | 5.0 | clear |
| 48 | 0.69 | 6.0 | 5.0 | 6.0 | clear |
| 49 | 0.70 | 6.0 | 4.0 | 8.5 | clear |
| 50 | 0.73 | 6.0 | 5.5 | 6.5 | clear |
| 51 | 0.70 | 6.0 | 4.0 | 6.0 | clear |
| 52 | 0.71 | 5.5 | 5.2 | 6.0 | clear |
| 53 | 0.70 | 5.5 | 4.0 | 6.0 | clear |
| 54 | 0.69 | 5.5 | 5.0 | 4.5 | clear |
| 55 | 0.69 | 6.0 | 5.0 | 6.0 | clear |
| 56 | 0.58 | 6.0 | 5.0 | 6.0 | clear |
| 57 | 0.74 | 5.5 | 5.0 | 6.0 | clear |
| 58 | 0.73 | 5.0 | 4.5 | 4.5 | clear |

TABLE 1-continued

| Ex. | Drop Tests | Cleaning Test Interior | Shell | Beef Tallow | Appearance at 100° F. (about 38° C.) for 2 weeks (Exs. 7–64) for 1 month (Exs. 1–6 & 65–122) |
|---|---|---|---|---|---|
| 59 | 0.72 | 5.0 | 4.5 | 5.0 | hazy |
| 60 | 0.72 | 6.0 | 4.5 | 5.0 | hazy |
| 61 | 0.92 | 5.0 | 4.5 | 5.0 | clear |
| 62 | 0.74 | 5.0 | 4.5 | 5.0 | clear |
| 63 | 0.72 | 5.5 | 4.0 | 5.0 | clear |
| 64 | 0.67 | 6.0 | 4.5 | 5.5 | clear |
| 65 | 0.77 | 6.5 | 5.9 | 6.8 | swirly |
| 66 | 0.84 | 7.0 | 5.5 | 5.0 | unstable |
| 67 | 0.80 | 6.0 | 7.0 | 6.0 | unstable |
| 68 | 1.03 | 7.0 | 6.5 | 4.5 | unstable |
| 69 | 0.93 | 7.0 | 5.5 | 7.0 | unstable |
| 70 | 0.92 | 7.0 | 5.0 | 5.5 | unstable |
| 71 | 1.02 | 6.0 | 5.0 | 4.5 | unstable |
| 72 | 0.89 | 7.0 | 6.5 | 6.0 | unstable |
| 73 | 0.90 | 7.0 | 6.5 | 4.0 | swirly/cloudy |
| 74 | 0.84 | 7.0 | 6.5 | 6.0 | unstable |
| 75 | 0.78 | 6.0 | 6.5 | 6.0 | slightly cloudy |
| 76 | 0.81 | 7.0 | 8.0 | 5.0 | cloudy |
| 77 | 0.92 | 6.0 | 7.0 | 5.5 | cloudy |
| 78 | 0.89 | 8.0 | 7.0 | 7.5 | unstable |
| 79 | 0.86 | 6.0 | 6.5 | 5.5 | unstable |
| 80 | 0.86 | 8.0 | 7.0 | 5.5 | unstable |
| 81 | 0.79 | 6.0 | 7.0 | 6.5 | unstable |
| 82 | 0.93 | 7.0 | 7.0 | 5.0 | unstable |
| 83 | 0.76 | 7.0 | 7.0 | 6.5 | swirly |
| 84 | 0.88 | 8.0 | 7.0 | 5.0 | unstable |
| 85 | 0.90 | 7.0 | 7.0 | 4.5 | unstable |
| 86 | 0.67 | 6.0 | 7.0 | 6.0 | slightly cloudy |
| 87 | 0.76 | 6.5 | 5.0 | 8.0 | slightly cloudy |
| 88 | 0.77 | 6.0 | 4.5 | 7.0 | swirly |
| 89 | 0.71 | NT | NT | NT | swirly |
| 90 | 0.73 | 6.5 | 6.0 | 7.0 | strands/swirly |
| 91 | 0.73 | 6.0 | 5.0 | 8.0 | clear |
| 92 | 0.73 | 7.0 | 6.5 | 6.0 | unstable |
| 93 | 0.73 | 6.5 | 6.0 | 6.5 | swirly |
| 94 | 0.73 | 6.0 | 5.0 | 5.5 | swirly |
| 95 | 0.71 | 6.5 | 5.0 | 4.0 | swirly |
| 96 | 0.66 | 6.0 | 8.0 | 7.0 | clear |
| 97 | 0.75 | 7.0 | 4.5 | 8.0 | unstable |
| 98 | 0.75 | 6.5 | 4.8 | 7.0 | strands/swirly |
| 99 | 0.80 | 7.0 | 6.5 | 7.0 | unstable |
| 100 | 0.79 | 6.5 | 6.0 | 5.5 | unstable |
| 101 | NT | NT | NT | NT | unstable |
| 102 | NT | NT | NT | NT | unstable |
| 103 | NT | NT | NT | NT | unstable |
| 104 | 0.73 | 6.5 | 6.0 | 5.5 | clear |
| 105 | 0.76 | 7.0 | 6.0 | 7.0 | unstable |
| 106 | 0.75 | 6.5 | 6.0 | 6.0 | swirly |
| 107 | 0.74 | 7.0 | 6.5 | 6.5 | swirly |
| 108 | 0.74 | 6.5 | 6.5 | 6.5 | swirly |
| 109 | 0.75 | 6.5 | 8.0 | 6.0 | swirly |
| 110 | 0.73 | 6.5 | 5.5 | 6.0 | unstable |
| 111 | 0.74 | 6.5 | 4.5 | 7.0 | slightly cloudy |
| 112 | 0.71 | 6.5 | 6.5 | 7.0 | swirly |
| 113 | 0.75 | 6.5 | 6.5 | 6.0 | oily/swirly |
| 114 | 0.71 | 6.5 | 6.0 | 7.0 | swirly |
| 115 | 0.82 | 6.5 | 7.0 | 6.0 | swirly |
| 116 | 0.86 | 7.0 | 6.5 | 6.5 | swirly |
| 117 | 0.84 | 7.0 | 6.5 | 7.0 | swirly |
| 118 | 0.80 | 6.0 | 7.0 | 7.0 | cloudy |
| 119 | 0.70 | 6.0 | 6.8 | 7.5 | unstable |
| 120 | NT | NT | NT | NT | unstable |
| 121 | 0.79 | 6.5 | 5.0 | 6.5 | clear |
| 122 | 0.76 | 6.0 | 6.5 | 6.5 | clear |

NT - not tested

TABLE 2

| Example | Sliding Drop Test (3 drops) |
|---|---|
| 1 | 4.5 |
| 2 | 4.5 |
| 3 | 4.5 |
| 4 | 3.0 |
| 5A | 4.5 |
| 6 | 3.0 |
| 7 | 3.0 |
| 18 | 3.4 |
| 31 | 1.7 |
| 42 | 3.0 |
| 55 | 3.5 |
| 56 | 3.5 |
| 61 | 1.8 |
| 65 | 3–3.5 |
| 86 | 3.5–4.0 |
| 96 | 3.5–4.0 |

Many of the formulations of this invention remained stable, i.e., without a substantial white cloudy or strand like appearance in a clear solution, even after storage at 100° F. for two weeks to a month. In general, the nonionic surfactants, and particularly the nonionic ethoxylated alcohols, tended to provide stable formulas. The amphoteric betaines, and particularly Lonzaine® CO (cocoamidopropyl betaine), also generally provided positive results. In addition, formulations using relatively long carbon chain amine oxides, such as Lonza Barlox® 6-S and Lonza Barlox® 18-S in combination with a glycolic acid system were found to be quite stable.

The results of the water drop test set forth in Table 1 shows that many of the formulations of this invention increased the hydrophobicity of the treated surface. Examples 2, 4, 18, 56, 86, 95, 96, 112 and 114 exhibited particularly strong hydrophobicity.

Notwithstanding a formulation's ability to deliver a protective silane coating and render a surface hydrophobic, the formulation should also have the ability to clean. The cleaning test results illustrated in Table 1, show that some of the formulations are particularly strong overall for each of the soil groups, while other formulations evidence strong cleaning properties for a particular soil group. Thus, the results of these tests indicate that the formulations of this invention are not only stable and provide a protective silane coating, but also provide effective cleaning efficacy, the scope of which can be modified depending on the nature of the formulation.

The results set forth in Table 2, also confirm that the formulations of Examples 1–7, 18, 42, 55, 56, 65, 86 and 96 rendered the surface of ceramic tiles treated with those formulations hydrophobic or water repellant.

Industrial Applicability

The cleaning formulation sof this invention are highly storage stable even when packaged in glass containers, and therefore conserve the active silane for attachment to treated surfaces. In addition, the method of applying the alkaline cleaning formulations of this invention may be advantageously used to clean and protect water covered surfaces with a minimal use of materials and effort.

Other variations and modifications of this invention will be obvious to those skilled in this art. This invention is not to be limited except as set forth in the following claims.

What is claimed is:

1. An acidic cleaning formulation for cleaning hard surfaces comprising:

(i) a hydrolyzed trialkoxysilane in an amount from about 0.00001 to about10 percent by weight of said formulation, wherein said hydrolyzed trialkoxysilane is formed in an aqueous emulsion from a hydrolyzable trialkoxysilane compound;

(ii) a surfactant in an amount from about 0.00001 to about 1 percent by weight of said formulation; and (iii) an alcohol having 1–12 carbon atoms, wherein the trialkoxysilane compound has the formula; $R^1$—$(CH_2)_p$—Si{(—O—$CH_2CH_2)_n$—$OR^2$}$_3$ wherein $R^1$ is selected from the group consisting of a perfluoroalkyl group of 3 to 18 carbon atoms or an alkyl group of 3 to 24 carbon atoms, and $R^2$ is independently an alkyl group having 1 to 3 carbon atoms, p is 0 to 4 and n is 2 to 10.

2. An acidic cleaning formulation according to claim 1, wherein said hydrolyzed trialkoxysilane is formed in an aqueous emulsion from said hydrolyzable trialkoxysilane compound emulsified in water with about 5 to 100 percent by weight of an emulsifier based on the weight of said hydrolyzable trialkoxysilane.

3. An acidic cleaning formulation according to claim 2, wherein said emulsifier is an ethoxylated $C_{8-18}$ amine salt.

4. An acidic cleaning formulation according to claim 1, wherein said surfactant is selected from the group consisting of nonionic surfactants, amphoteric betaines, amphoteric sultaines, imidazoline amphoterics, amine oxides, quaternary cationics, dialkoxy alkyl quatemaries and mixtures thereof.

5. An acidic cleaning formulation according to claim 1, wherein said alcohol is selected from the group consisting of mono-hydric alcohols, dihydric alcohols, tri-hydric alcohols and mixtures thereof.

6. An acidic cleaning formulation according to claim 1, further comprising an acid in an amount effective to provide said formulation with a pH less than 7.0 wherein said acid is selected from the group consisting of glycolic acid, lactic acid, citrc acid, gluconic acid, sulfamic acid and acetic acid.

7. An acidic cleaning formulation according to claim 1, wherein the pH of said formulation is about 0.5 to about 6.95.

8. An acidic cleaning formulation according to claim 1, wherein said alcohol is selected from the group consisting of isopropanol, hexanol and mixtures thereof.

9. An acidic cleaning formulation according to claim 1, further comprising a glycol ether.

10. A method for cleaning and modifying a hard surface covered by water comprising the step of applying an acidic cleaning formulation according to claim 1, to water contacting said hard surface in an amount effective to modify said hard surface by attachment of said surface modification agent to said surface.

11. A method according to claim 10, wherein the concentration of said hydrolyzed trialkoxysilane in said water is from about 0.10 to about 10,000 ppm.

12. An acidic cleaning formulation according to claim 1, further comprising a siloxane in an amount effective to reduce autophobicity of the cleaning formulation.

13. An acidic cleaning formulation for cleaning hard surfaces comprising:

(a) a surface modification agent selected from the group consisting of:

(i) a hydrolyzed trialkoxysilane in an amount from about 0.00001 to about 10 percent by weight of the formulation and (ii) a hydrolyzable quaternary silane in an amount from about 0.00001 to about 10 percent by weight of the formulation;

(b) a surfactant in an amount from about 0.0001 to about 10 percent by weight of the formulation, provided that if the surface modification agent is a hydrolyzable quaternary silane then the surfactant is not a quaternary ammonium compound or a sulfobetaine;

(c) an alcohol having 1 to 12 carbon atoms;

(d) a siloxane in an amount effective to reduce autophobicity of the cleaning formulation; and p1 (e) water.

14. The formulation of claim 13 wherein:

the surface modification agent is a hydrolyzed trialkoxysilane compound having the formula: $R^1$—$(CH_2)_p$—Si{(—O—$CH_2CH_2)_n$—$OR^2$}$_3$ wherein $R^1$ is selected from the group consisting of a perfluoroalkyl group of 3 to 18 carbon atoms or an alkyl group of 3 to 24 carbon atoms, and $R^2$ is independently an alkyl group having 1 to 3 carbon atoms, p is 0 to 4 and n is 2 to 10.

15. The formulation of claim 14 wherein:

the hydrolyzed trialkoxysilane compound is formed in an aqueous emulsion from the hydrolyzable trialkoxysilane compound emulsified in water with about 5 to 100 percent by weight of an emulsifier based on the weight of the hydrolyzable trialkoxysilane compound.

16. The formulation of claim 15 wherein:

the emulsifier is an ethoxylated $C_{8-18}$ amine salt.

17. The formulation of claim 15 wherein:

the concentration of the hydrolyzed trialkoxyrilane compound in the water is from about 0.1 to about 10,000 ppm.

18. The formulation of claim 14 further comprising a glycol ether.

19. The formulation of claim 14 wherein:

the surfactant is selected from the group consisting of nonionic surfactants, amphoteric betaines, amphoteric sultaines, imidazoline amphoterics, amine oxides, quaternary cationics, dialkoxy alkyl quaternaries and mixtures thereof.

* * * * *